US006022368A

United States Patent [19]

Gavronsky et al.

[11] Patent Number: 6,022,368

[45] Date of Patent: Feb. 8, 2000

[54] ACUPUNCTURE METHOD AND DEVICE

[76] Inventors: Stas Gavronsky, 39 Wayland Hills Rd.; Igor Burdenko, 34 Joyce Rd., both of Wayland, Mass. 01778

[21] Appl. No.: 09/201,069

[22] Filed: Nov. 30, 1998

[51] Int. Cl.[7] .......... A61B 17/34

[52] U.S. Cl. .......... 606/189

[58] Field of Search .......... 606/189, 204; 604/46, 47

[56] References Cited

U.S. PATENT DOCUMENTS 5,089,001 2/1992 Hwang .......... 606/189

5,792,171 8/1998 Burdenko et al. .......... 606/189

*Primary Examiner*—Michael H. Thaler

[57] ABSTRACT

An acupuncture method and a device for combining acupuncture with therapeutic physical exercises and/or water therapy. The device comprises a convex enclosure made of a resilient material such as rubber, which is capable of resuming initial full convex shape after being subjected to vertical downward pressure, and a small acupuncture needle the upper portion of which is molded into the enclosure. The open end face of the enclosure is sealed with an adhesive tape which seals the interior of the enclosure. The tip of the needle protrudes through this adhesive tape. In operation, the device is attached to the skin of a patient at the site of particular acupuncture point, and the acupuncturist applies a to the needle via the top of the dome-like enclosure so that the tip of the needle penetrates the skin of the patient at the site of acupuncture point. The patient starts to perform therapeutic exercises on land or in the water, experiencing barely noticeable sensation. This stimulation, though, can be easily increased by therapist through application of some downward pressure on the top of the enclosure. After a certain time, the enclosure flattened by the pressure will restore its initial convex shape.

24 Claims, 1 Drawing Sheet

ACUPUNCTURE METHOD AND DEVICE

FIELD OF THE INVENTION

The present invention relates to the field of nontraditional medicine and more particularly to an acupuncture method and device.

BACKGROUND OF THE INVENTION

Acupuncture is a method of encouraging the body to promote natural healing and to improve functioning. This is done by inserting needles and applying heat or electrical stimulation at very precise acupuncture points.

The classical Chinese explanation is that channels of energy run in regular patterns through the body and over its surface. These channels, called meridians, are like rivers flowing through the body to irrigate and nourish the tissues. Blood flow and nervous pulses also follow meridians to run through the body to various parts, structures and organs. An obstruction in the movement of these energy rivers is like a dam that backs up the flow in one part of the body and restricts it in others. Any obstruction and blockages or deficiencies of energy, blood and nervous pulses would eventually lead to disease.

The meridians can be influenced by needling the acupuncture points: the acupuncture needles unlock the obstruction at the dams, and reestablish the regular flow through the meridians. Acupuncture treatment can, therefore, help the body's internal organs to correct imbalances in their digestion, absorption, and energy production activities, and in circulation of their energy through the meridians.

Modern science explains the functions of acupuncture in two major ways:

1. Needling the acupuncture points stimulates the nervous system to release chemicals in the muscles, spinal cord, and brain. These chemicals will either change the sensation of pain, or they will trigger the release of other chemicals and hormones which influence the body's own internal regulating system.

2. Modern science reveals that the very basic unit of the body is cell. Cells' movement follow the movement of electrons. The electrons inside the cell act according to their own regular patterns. We call all these electrons in a living body bioelectrons.

Energy flow in the meridians is the direct or indirect transportation of bioelectrons. Meridians are the pathways where bioelectrons move more frequently than in other parts of the body. When positive and negative charges in the bioelectronic movements are not balanced, the cells would act abnormally.

All the external factors, such as mechanical, physical, chemical, biological and internal factors such as mental, hereditary, constitutional can cause and force the body's bioelectrical movement turn to imbalance and would lead to a disease.

Acupuncture or needle therapy for treating various ailments have been known for at least four thousand years. Different materials, including stone, wood and, in recent years, metal were used for manufacturing acupuncture needles. Twentieth century discoveries in biomedicine gave better understanding about transmission of the infectious diseases. Based on this knowledge, new much stricter requirements for safety and sterility during acupuncture procedure were imposed. Modern day acupuncturists in the USA and other developed countries use sterile, disposable needles made of stainless steel or, sometimes, other metals. In 1996, FDA has approved acupuncture needles as medical equipment, acknowledging safety and effectiveness of the procedure. Many hospitals have started incorporating acupuncture as part of their services over last years.

On the other hand, the healing effect of water therapy is known since ancient times, and at the present time water therapy finds ever growing application for treating various diseases, as well as for physical exercises, rehabilitation of athletes and patients after surgical operations, traumas, etc. Treatment in water may be carried out even without physical exercises or movements, but rather solely due to variation of water temperature. Such treatment is based on specific physiological responses water produces in patients. These physiological responses are the following: hydrostatic pressure evens out tactile input, helps reduce tactile defensiveness due to generalized constant sensory input which helps "turn off" the rectile system; warm water promotes inhibition of spastic muscles, promotes relaxation and decreases pain, increases superficial and peripheral circulation, intensifies blood supply to muscles, decreases joint compression force, prepares connective tissue for stretching, increases body temperature, and produces many other useful effects.

For the acupuncture prospective, various types of temperature modifying tools have been used in acupuncture for centuries. They were used to enhance the therapeutic effect of the acupuncture treatment. External application of heat and heat generating herbs were utilized to produce a physiological response to that obtained during treatment with warm water. A special herb, *Artemisia Vulgaris*, which is burnt on or over the skin, infrared heaters, herbal compresses with warming properties are among popular acupuncturist tools for altering temperature. At the same time, if a patient is placed in a tub in which temperature can be controlled, a guaranteed systemic response in the patient is assured, and the bodily processes can be shifted in a desired direction. A good example from the clinical practice is the acupuncture treatment of the muscular and skeletal problems. The muscular and skeletal conditions, with damage limited primarily to soft tissues, respond extremely well to a combination of acupuncture with heat. Both methods enhance the blood circulation, relax muscles and tendons, increase the metabolic rate, and promote healing. Low back pains, sprains, strains, repetitive motion disorders, and many others fall into this category.

It was, however, impossible to utilize acupuncture under water because of hygienic problems, problems of sterility and, therefore, a risk of infection through the use of conventional acupuncture techniques.

For the solution of the above problem the applicant has developed a method and apparatus for underwater needle therapy which are described in U.S. Pat. No. 5,792,171 issued in 1998. This method and apparatus advantageously use a synergistic effect resulting from a combined use of acupuncture and a water therapy treatment. The device for carrying out the method comprises an enclosure which is sealed at one end and has a flange on the opposite open end. The sealed end has a resilient tip and supports a sterile acupuncture needle inside the enclosure. The flange has an adhesive outer tape for sealingly attaching the device to the skin of a patient in the area of an acupuncture point. The acupuncture needle is guided through a longitudinal channel of a guide tube inserted into the enclosure and can be brought into contact with the skin of the patient by pushing on the aforementioned resilient tip.

Although the underwater acupuncture device of U.S. Pat. No. 5,792,171 appeared to be efficient due to combination of acupuncture treatment with hydrotherapy, it is still complicated in construction and is intended for use only when a patient is in a static state. This is because traditional needles are relatively long and will not be secured in place if the patient moves or make exercise. It is especially true for movement of the patient with needles under water, since water exerts an increased resistance to such movements and will facilitate disconnection of the needles from the patient's skin.

OBJECTS OF THE INVENTION

It is an object of the invention to provide a method and apparatus for combining acupuncture with therapeutic physical exercises. Another object is to provide acupuncture needles which are suitable for acupuncture in combination with exercises or with movement under water. Still another object is to provide an acupuncture device which is simple in construction, easy to use, convenient for storage in a sterilized state, and stable when inserted into the patient's skin.

SUMMARY OF THE INVENTION

An acupuncture method and a device for combining acupuncture with therapeutic physical exercises and/or water therapy. The device comprises a convex enclosure made of a resilient material such as rubber, which is capable of resuming initial full convex shape after being subjected to vertical downward pressure, and a small acupuncture needle the upper portion of which is molded into the enclosure. The open end face of the enclosure is sealed with an adhesive tape which seals the interior of the enclosure. The tip of the needle protrudes through this adhesive tape. In operation, the device is attached to the skin of a patient at the site of particular acupuncture point, and the acupucturist applies a to the needle via the top of the dome-like enclosure so that the tip of the needle penetrates the skin of the patient at the site of acupuncture point. The patient starts to perform therapeutic exercises on land or in the water, experiencing barely noticeable sensation. This stimulation, though, can be easily increased by therapist through application of some downward pressure on the top of the enclosure. After a certain time, the enclosure flattened by the pressure will restore its initial convex shape.

DETAILED DESCRIPTION OF THE INVENTION

Figure 1:
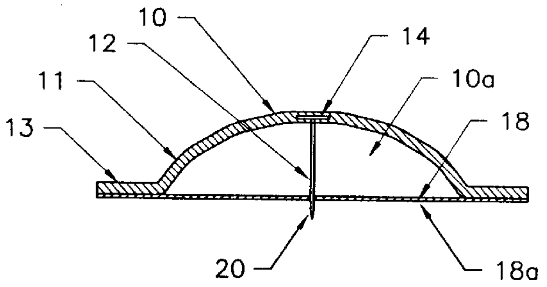

An acupuncture device of the invention is shown in FIG. 1 which is a sectional view of the device. The device consists of an enclosure 10 made of resilient material which is capable of resuming initial full convex shape after being subjected to vertical downward pressure. This may be, e.g., rubber. Enclosure 10 has a dome-like portion 11 with an interior cavity 10*a* and a flange portion 13 that may be molded integrally with dome portion 11. An outer surface of flange portion 13 is coated with an adhesive tape 18 which is attached to the flanged portion and has an adhesive material 18*a* on the exposed part of the tape. A small acupuncture needle 12 (typically, 3–8 mm-long) has a tail portion 14 which is flat and is molded into enclosure 10 at the top of the convex profile, so that the main part of the needle is located inside interior cavity 10*a*. On the end opposite to flat upper portion 14, small acupuncture needle 12 has a tip 16 which protrudes from cavity 10*a* through adhesive tape 18. Adhesive tape 18 seals interior 10*a* of enclosure 10.

Figure 2:
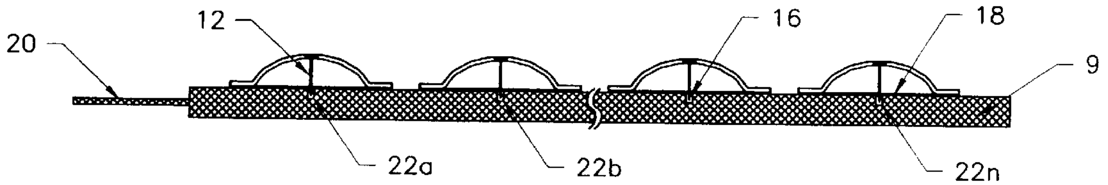

FIG. 2 illustrates a device for storing acupuncture needles 12 in a sterilized state prior to use. The device comprises a wooden or plastic block 20 with recesses 22*a*, 22*b*, . . . 22*n*. The depth of these recesses exceeds the length of tip 16 which protrudes through adhesive tape 18. During storage, tips 16 of needles 12 are inserted into recesses 22*a*, 22*b*, . . . 22*n* of storage block 20 and are fixed to the block by adhesive tape 18. It is assumed that all elements, including adhesive tape 18, acupuncture needles 12, recesses 22*a*, 22*b*, . . . 22*n*, and attachable areas of storage block 20 are sterile and biologically safe. Adhesive tape 18 should be made of a water-proof material for keeping needle 12 isolated from water environment during underwater procedures.

Figure 3:
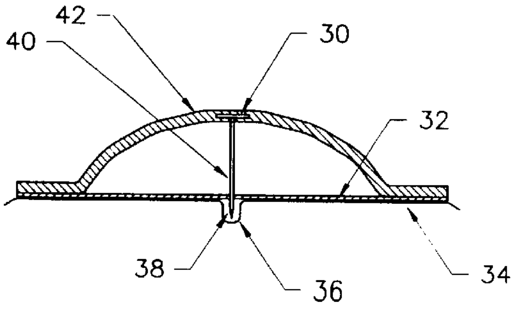

FIG. 3 shows an embodiment of an acupuncture device 30 of the invention in which the adhesive material 32 is coated with a protective peelable tape or film 34. Protective tape 34 may have a protective cap 36 for protecting a tip 38 of an acupuncture needle 40 which is attached to an enclosure 42 of the device in the same manner as in the previous embodiment of the invention.

OPERATION OF THE DEVICE OF THE INVENTION

At the beginning of acupuncture procedure, a small acupuncture needle device, consisting of enclosure 10, needle 12, and adhesive tape 18, is removed from the storage board by peeling adhesive tape 18 off from storage block 20 and is placed on the patients skin (not shown) at the site of particular acupuncture point. It is assumed that acupuncture point has been treated with alcohol prior to the procedure, and all necessary clean needle technique requirements were implemented.

At the beginning of an acupuncture procedure, under effect of the pressure applied by a therapist to the needle, tip 16 of needle 10 penetrates the skin of a patient at the site of acupuncture point. Tip 16, which is only couple millimeters long, exhibits some very mild stimulation on the acupuncture point. Patient starts to perform therapeutic exercises on land or in the water, experiencing barely noticeable sensation. This stimulation, though, can be easily increased by therapist through application of some downward pressure on the top of enclosure 10. At this moment, enclosure 10 yields to exhibited pressure and flattens, while bringing the top portion 14 of small acupuncture needle 10 closer to the skin. As a result of this action, longer portion of needle 12 is now inserted into the point; stimulation increases. After stimulating the acupuncture point as necessary, the patient resumes exercises under supervision of the therapist. Without the pressure, enclosure 10 resumes its normal convex shape, which brings acupuncture needle 12 to the very surface of patient's skin (initial position).

Same device(s) can be left on a patient between office visits. The patient would stimulate specific points as instructed by the acupuncturist. This helps to control pain and discomfort between sessions. During a water procedure certain amount of air is trapped inside enclosure 10. However, due to a small size of the device and the ability of enclosure 10 to flatten, there is enough space to accommodate air pressure inside enclosure 10 during stimulation.

Acupuncture device 30 shown in FIG. 3 operates in the same manner as the device of FIGS. 1 and 3 with the exception that the device can be stored without block 20 and that, prior to application to the patient's skin, adhesive material 32 should be exposed by removing peelable tape 34.

Thus it has been shown that the invention provides a method and a device for combining acupuncture with therapeutic physical exercises on land or under water. The device is simple in construction, easy to use, convenient for storage in a sterilized state, and stable when inserted into the patient's skin.

Although the invention has been described with reference to specific constructions and steps of the method, it is understood that these constructions and technological steps were given only as examples which do not limit the scope of application of the present invention. For example, the adhesive tape may be coated with a peelable protective layer instead of using a wooden or plastic block 20, and the tip of the needle can be covered with a removable protective sterilized cap, or an integral peelable structure may cover the adhesive surface of the enclosure flange and the needle tip. The enclosure can be made of rubber or plastic. Protective cap 36 can be made separately from peelable tape 34.

We claim:

1. A method of acupuncture treatment comprising:

providing an acupuncture device which consists of a convex enclosure with means for attaching said acupuncture device to the skin of a patient, and an acupuncture needle located inside said convex enclosure and attached to said enclosure at a needle attachment area, said convex enclosure being made of a resilient material capable of restoring its unstressed initial shape after being deformed by pressure applied to said enclosure, the tip of said acupuncture needle projecting through said means for attaching when said convex enclosure is in its unstressed, initial state;

attaching said acupuncture device to the skin of the patient, in an acupuncture site by means of said means for attaching thus inserting said needle into the patient's body to a first depth;

further inserting said needle into the patient's body by pressing on said needle attachment area of said convex enclosure;

releasing the pressure from said needle attachment area and allowing said enclosure to restore its initial shape which causes said needle to move back to its original position to said first depth; and maintaining said needle in the patients skin after said enclosure restored its initial shape and while said patient is in a mobile state.

2. The method of claim 1, wherein said enclosure has an interior in which said needle is located, said interior being sealed with said means for attaching, said needle being sterile, including said tip of said acupuncture needle which projects through said means for attaching.

3. The method of claim 2, further comprising the step of holding said tip of said acupuncture needle in a sterile environment during storage of said acupuncture device.

4. The method of claim 3, wherein said enclosure is made of a material selected from a group consisting of resin and rubber, said means for attaching said acupuncture device to the skin of a patient comprising an adhesive tape attached to said enclosure, said adhesive tape having an adhesive surface on the side of said adhesive tape which is exposed, said adhesive surface being closed during storage of said acupuncture device and can be exposed for attachment to the patient's skin.

5. The method of claim 4, further comprising the step of causing said patient to perform physical exercises while said acupuncture device is maintained on the patient's skin.

6. The method of claim 4, wherein said sterile environment is a block of a solid material with a recess for receiving said tip with the depth of said recess being greater than the protruding length of said tip, said adhesive surface of said adhesive tape being attached to said block so that said tip is kept in said cavity.

7. The method of claim 3, wherein said needle has a length of 3 to 8 mm.

8. The method of claim 1, wherein said enclosure is made of a material selected from a group consisting of resin and rubber, said means for attaching said acupuncture device to the skin of a patient comprising an adhesive tape attached to said enclosure, said adhesive tape having an adhesive surface on the side of said adhesive tape which is exposed, said adhesive surface being closed during storage of said acupuncture device and can be exposed for attachment to the patient's skin.

9. The method of claim 1, wherein said step of pressing on and releasing said needle attachment area of said convex enclosure is repeated more than once while said acupuncture device is maintained on the patient's skin.

10. The method of claim 1, further comprising the step of causing said patient to perform physical exercises while said acupuncture device is maintained on the patient's skin.

11. The method of claim 10, wherein said needle has a length of 3 to 8 mm.

12. The method of claim 1, further comprising the step of subjecting said patient to hydrotherapeutic treatment with said acupuncture device being under water.

13. The method of claim 9, wherein said hydrotherapeutic treatment is combined with movements of said patient.

14. The method of claim 13, wherein said movements are physical exercises.

15. The method of claim 1, wherein said needle has a length of 3 to 8 mm.

16. An acupuncture device comprising:

a dome-shaped enclosure having an interior cavity, an open side, and a closed side;

means for attaching said acupuncture device to the skin of a patient from said open side;

an acupuncture needle having a tip, a tail portion and a length of 3 to 8 mm, said needle being located in said interior cavity, said tail portion being attached to said enclosure at said closed side, said convex enclosure being made of a resilient material capable of restoring its unstressed initial shape after being deformed by pressure applied to said closed side of said enclosure, said tip of said needle projecting through said means for attaching when said convex enclosure is in its unstressed, initial state.

17. The device of claim 16, wherein said interior cavity is sealed with said means for attaching, said needle, including said tip of said acupuncture needle which projects through said means for attaching, being sterile.

18. The device of claim 17, wherein said tip of said acupuncture needle is kept in a sterile environment during storage of said acupuncture device by protective means.

19. The device of claim 18, wherein said enclosure is made of a material selected from a group consisting of resin and rubber, said means for attaching said acupuncture device to the skin of a patient comprising an adhesive tape which has an exposed surface and is attached to said open side of said enclosure, said adhesive tape having an adhesive material on said exposed surface, said adhesive material being closed during storage of said acupuncture device and can be exposed for attachment to the patient's skin.

20. The device of claim 19, wherein said sterile environment is a block of solid material with a recess for receiving said tip with the depth of said recess being greater than the protruding length of said tip, said adhesive material of said adhesive tape being attached to said block so that said tip is kept in said cavity.

21. The device of claim 16, wherein said enclosure is made of a material selected from a group consisting of resin and rubber, said means for attaching said acupuncture device to the skin of a patient comprising an adhesive tape which has an exposed surface and is attached to said open side of said enclosure, said adhesive tape having an adhesive material on said exposed surface, said adhesive material being closed during storage of said acupuncture device and can be exposed for attachment to the patient's skin.

22. The device of claim 21, wherein said tail portion of said needle is made flat and is molded into the material of said enclosure.

23. The device of claim 21, wherein said enclosure has a flange on said open side, said adhesive tape being attached to said flange and said adhesive material being covered by a removable means.

24. The device of claim 23, wherein said removable means is a peelable tape.

* * * * *